US00PP11239P

United States Patent [19]

Boeder

[11] Patent Number: Plant 11,239

[45] Date of Patent: Feb. 22, 2000

[54] CHRYSANTHEMUM PLANT NAMED 'ROSELLA'

[75] Inventor: Mark Boeder, West Wittering, United Kingdom

[73] Assignee: Cleangro Limited, United Kingdom

[21] Appl. No.: 09/038,767

[22] Filed: Mar. 11, 1998

[51] Int. Cl.[7] ..... A01H 5/00

[52] U.S. Cl. ..... Plt./292

[58] Field of Search ..... Plt./287, 291, 292, Plt./293

[56] References Cited

PUBLICATIONS

UPOU–ROM, 1998/Apr., Plant Variety Database, GTI Jouve Retrieval Software, citation for 'T26–92', GB PBR01505169.

*Primary Examiner*—Howard J. Locker
*Attorney, Agent, or Firm*—Christie, Parker & Hale, LLP

[57] ABSTRACT

A new plant variety of Chrysanthemum producing pink flowers with coral centers.

2 Drawing Sheets

BACKGROUND OF THE INVENTION

The present invention is directed to a new and distinct variety of Chrysanthemum botanically classified as *Dendranthema grandiflora*. The varietal denomination of the new Chrysanthemum is 'Rosella'.

The female parent of the new variety is the variety known as 'Subito' and the male parent is an undistributed, unnamed seedling identified as 'G34C7'. The new variety has been asexually reproduced by vegatative cuttings in Ventura County, Calif. and the distinguishing characteristics are retained through successive generations of asexual reproduction.

SUMMARY OF THE INVENTION

'Rosella' is a pot type Chrysanthemum plant variety that produces pink flowers with a coral center and a compact growth habit.

COMPARISON WITH PARENT

'Rosella' differs from the female parent in producing flowers of different color.

BRIEF DESCRIPTION OF ILLUSTRATIONS

The accompanying photographs show flowers on a plant of a typical specimen of the new variety with colors being as nearly true as possible with illustrations of this type.

DESCRIPTION OF THE PLANT

Figure 1:
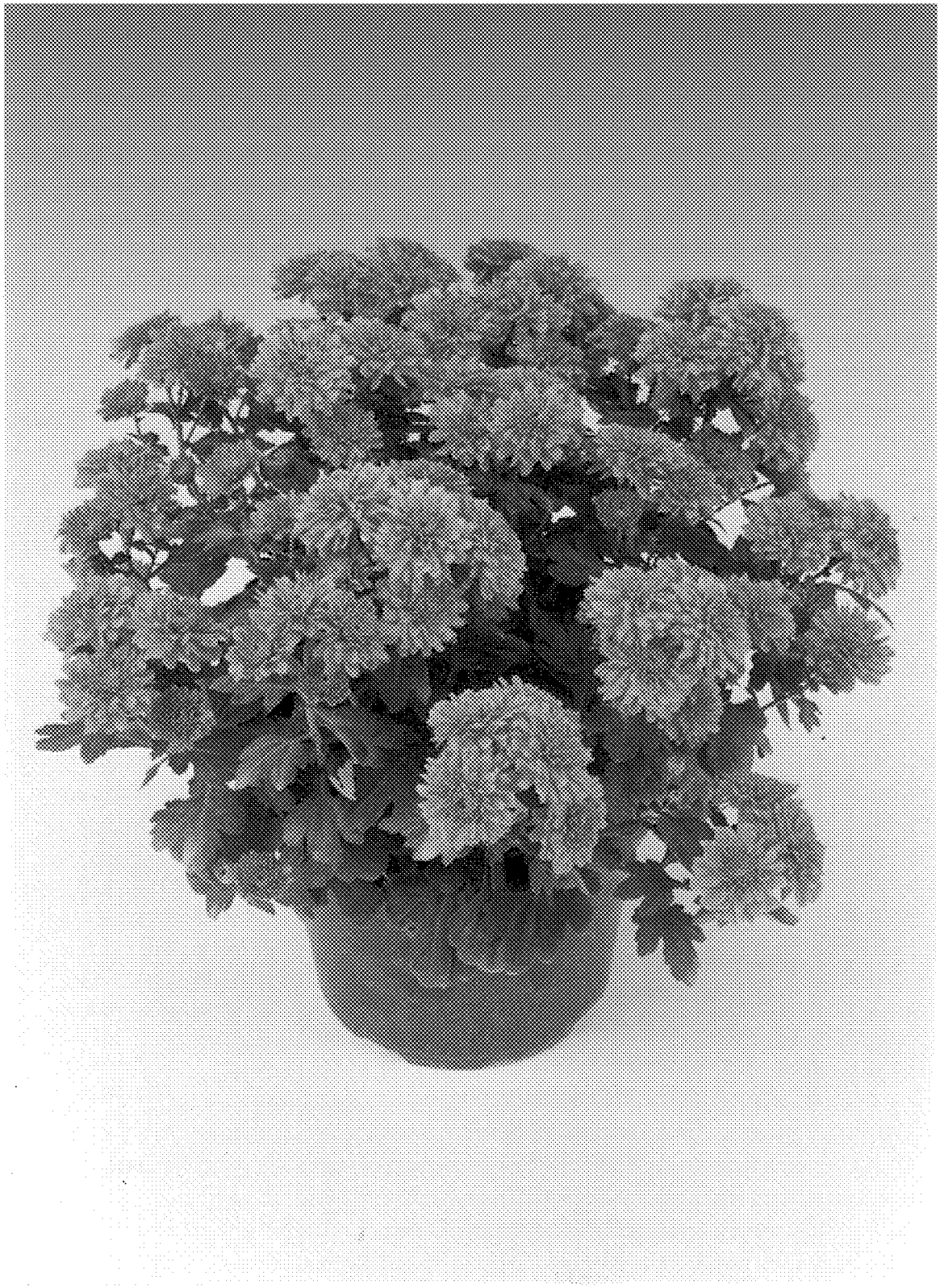
FIG. 1 is a whole plant view of the new cultivar grown in a pot.
Figure 2:
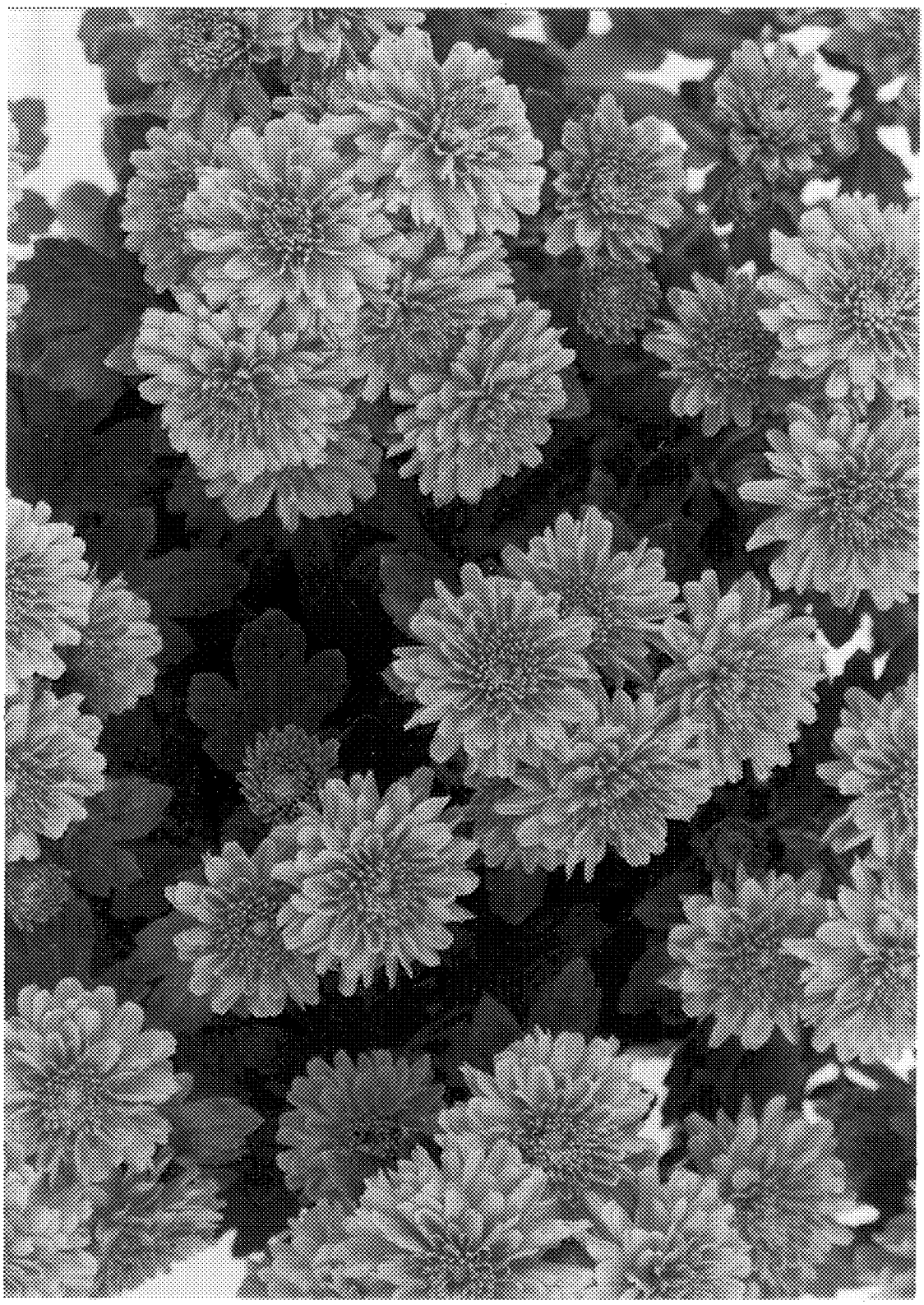
FIG. 2 is a closer view, showing inflorescence and foliage characteristics of the new cultivar in greater detail.

The following description of the new variety is of specimens grown in a greenhouse in Ventura County, Calif., in the month of October. 'Rosella' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once ten days after planting which results in about 3 to 4 breaks per pinch. It has been observed that the shelf life of 'Rosella' is about 23 days with the response time of about 7 weeks. No treatment with growth retardant is required. Useful growing conditions include night temperatures of about 64°–66° F., day temperatures of about 80°–85° F. and about 5,000 foot-candles of light.

Plant:
- *Habit.*—Compact.
- *Height.*—About 18 cm.
- *Number of breaks from pinch.*—About 3 to 4.
- *Length of lateral branches.*—About 14 cm.
- *Stem color.*—Near 138B.

Foliage:
- *Leaf arrangement.*—Alternate.
- *Number of leaves per lateral branch.*—About 15 fully expanded mature leaves.
- *Leaf size.*—Length: About 6 cm. Width: About 3.5 cm.
- *Leaft shape.*—Ovate.
- *Attachment.*—Petioled.
- *Leaf apex.*—Obtuse.
- *Base.*—Tapered.
- *Margin.*—Palmately lobed with infrequent serrations.
- *Aspect.*—Flat.
- *Surface.*—Top: Lightly pubescent. Bottom: Pubescent.
- *Petiole length.*—About 1.5 cm.
- *Color.*—Near 138B.
- *Leaf color.*—Mature leaf: Top: Near 137A. Bottom: Near 137C. Young Leaf: Top: Near 137B. Bottom: Near 137C.

Flower:
- *Inflorescence form.*—Cyme.
- *Flower form.*—Decorative.
- *Number of blooms per branch.*—About 6.
- *Diameter of fully expanded bloom.*—About 4 cm.
- *Depth of fully expanded bloom.*—About 1.5 cm.
- *Sepal number.*—About 40.
- *Peduncle.*—Length: Terminal peduncle about 3 cm, lowermost peduncle about 6 to 7 cm. Color: Near 138B.
- *Flower bud.*—Diameter: About 1 cm. Height: About 0.8 cm.
- *Ray florets.*—Number per flower: About 150. Texture: Matte. Shape: Oblanceolate. Apex: Obtuse. Base: Tapered. Margin: Entire. Aspect: Flat when mature. Length: About 1.8 cm. Width: About 0.6 cm.
- *Disc florets.*—Number per flower: About 15. Texture: Shiny. Shape: Cylindric. Margin: Entire. Length: About 0.4 cm. Width: About 0.1 cm.

*Fragrance.*—Strong, musky scent.

Flower color:

*General flower description.*—Rose pink with coral, near 39A. appearance at center.

*Ray florets, top side.*—Immature: Near 39A. Mature: Near 51C. Fading: Near 51C.

*Ray floret, under side.*—Immature: Near 37A. Mature: Near 51D. Fading: Near 51D.

*Disc florets.*—Mature: Near 1D, with 13A tip.

*Changes as the flower ages.*—Color lightens slightly; capitulum form remains flat.

Reproductive organs:

*Ray Florets.*—Pistillate. Stigma shape: Forked. Stigma color: Near 7A. Style length: About 0.4 cm.

*Disc Florets.*—Stigma shape: Forked. Stigma color: Near 12A. Style length: About 0.3 cm. Stamen number: About 5. Anther length: 0.15 cm. Pollen color: Near 13A. Pollen quantity: Abundant.

What is claimed is:

1. A new and distinct Chrysanthemum plant of the variety substantially as herein shown and described.

* * * * *